(12) United States Patent
Cornish et al.

(10) Patent No.: US 7,202,287 B2
(45) Date of Patent: Apr. 10, 2007

(54) METHOD AND COMPOSITIONS

(75) Inventors: Alexander Cornish, Manchester (GB); David John Hodge, Manchester (GB); Emerentiana Sianawati, New Castle, DE (US); Paula Louise McGeechan, Manchester (GB)

(73) Assignees: Arch Chemicals, Inc., Norwalk, CT (US); Arch UK Biocides Limited, West Yorkshire (GB)

( * ) Notice: Subject to any disclaimer, the term of this patent is extended or adjusted under 35 U.S.C. 154(b) by 181 days.

(21) Appl. No.: 10/362,450

(22) PCT Filed: Oct. 5, 2001

(86) PCT No.: PCT/GB01/04425

§ 371 (c)(1),
(2), (4) Date: Feb. 25, 2003

(87) PCT Pub. No.: WO02/28952

PCT Pub. Date: Apr. 11, 2002

(65) Prior Publication Data

US 2003/0187095 A1     Oct. 2, 2003

(30) Foreign Application Priority Data

Oct. 6, 2000     (GB) ................. 0024529.0

(51) Int. Cl.
C09D 5/14     (2006.01)
C08K 5/47     (2006.01)
(52) U.S. Cl. .......................... 523/122; 524/84
(58) Field of Classification Search ............. 523/122; 524/84
See application file for complete search history.

(56) References Cited

U.S. PATENT DOCUMENTS

| | | | |
|---|---|---|---|
| 3,517,022 A | 6/1970 | Miller et al. ............ | 260/304 |
| 3,523,121 A | 8/1970 | Lewis et al. ............. | 260/306.7 |
| 5,464,851 A * | 11/1995 | Morpeth ................... | 514/373 |
| 6,830,758 B2 * | 12/2004 | Nichols et al. ............ | 424/443 |

FOREIGN PATENT DOCUMENTS

| | | |
|---|---|---|
| EP | 0 513 637 A2 | 11/1992 |
| GB | 702268 | 1/1954 |
| JP | 11071210 A | 3/1999 |

* cited by examiner

Primary Examiner—Kriellion Sanders
(74) Attorney, Agent, or Firm—Morgan Lewis & Bockius LLP

(57) ABSTRACT

The invention relates to a method for inhibiting the growth of microorganisms in a latex, especially a sterically stabilised or cationic stabilised latex and to a composition for use in the method comprising a polymeric biguanide and an isothiazolinone of the Formula (1).

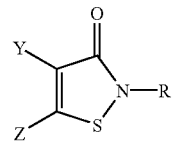

Formula (1)

wherein:
R is H, alkyl, cycloalkyl or aralkyl; and
Y and Z each independently are H, halogen or $C_{1-4}$-alkyl or Y and Z together with the carbon atoms to which they are attached form an optionally substituted 5 or 6 membered ring.

12 Claims, 4 Drawing Sheets

FIGURE 1: Isobologram Showing Activity of Mixtures of BIT and Vantocil$^{RTM}$ IB (PHMB) Against *Ps. aeruginosa*
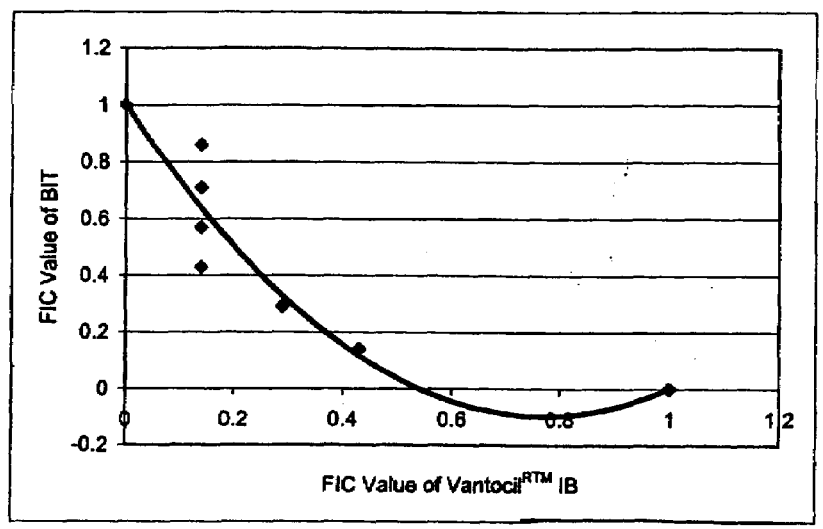
FIGURE 2: Isobologram Showing Activity of Mixtures of Butyl BIT and Vantocil$^{RTM}$ IB (PHMB) Against *Ps. aeruginosa*
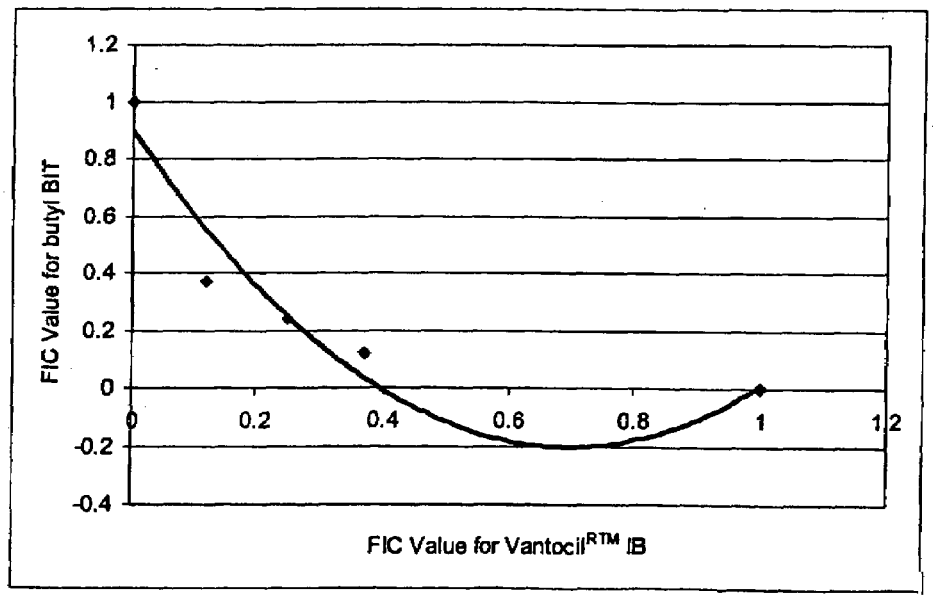

FIGURE 3: Isobologram Showing Activity of Mixtures of n-Butyl BIT and Vantocil$^{RTM}$ IB (PHMB) against *Aspergillus Niger*
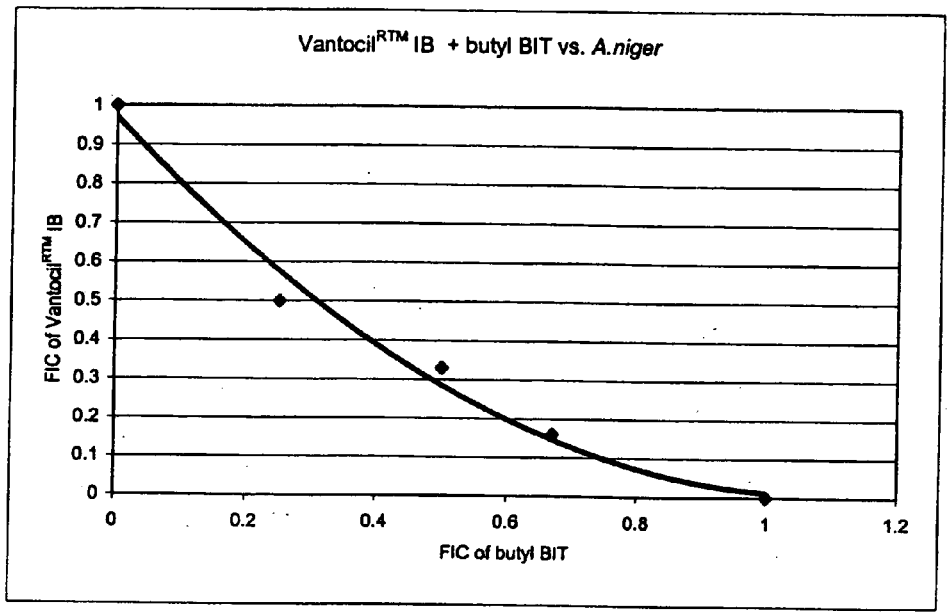
FIGURE 4: Isobologram Showing Activity of Mixtures of Vantocil$^{RTM}$ IB (PHMB) and CMIT/MIT in VAE Against *Acetobacter*
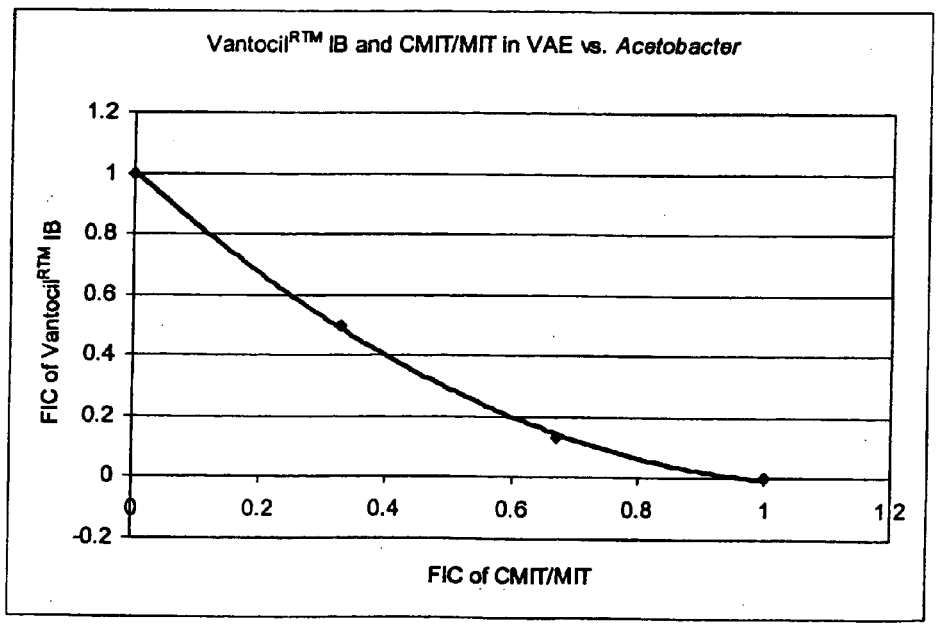

FIGURE 5: Isobologram Showing Activity of Mixtures of Vantocil[RTM] IB (PHMB) and MIT in VAE Against *Acetobacter*
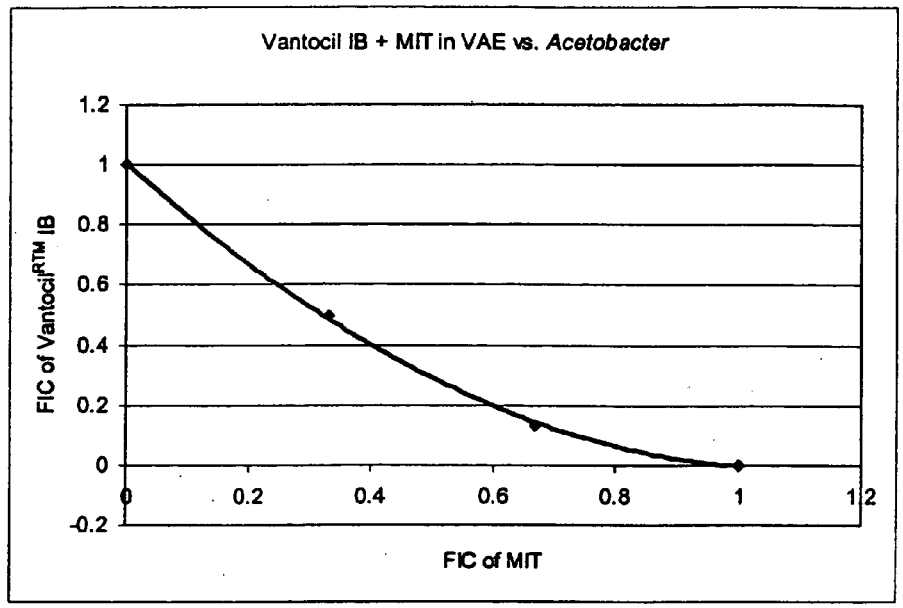
FIGURE 6: Isobologram Showing Activity of Mixtures of Vantocil[RTM] IB (PHMB) and BIT in VAE Against *Acetobacter*
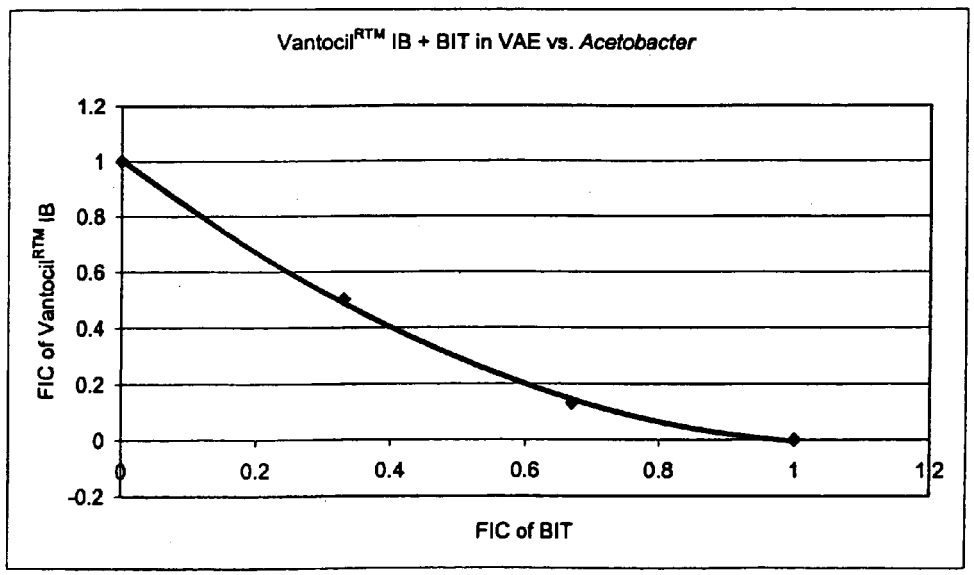

FIGURE 7: Isobologram Showing Activity of Mixtures of Vantocil[RTM] IB (PHMB) and Butyl BIT in VAE Against *Acetobacter*
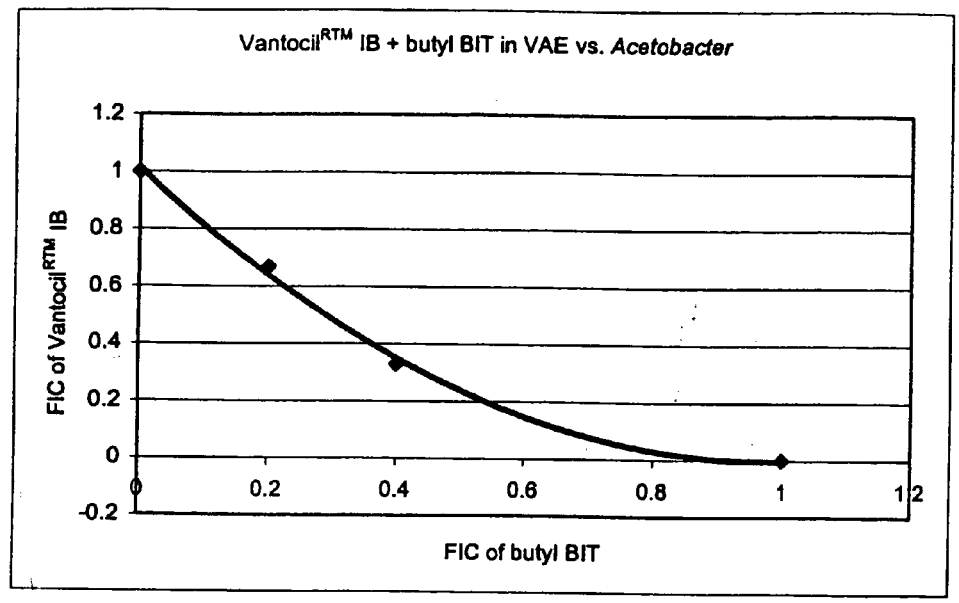

METHOD AND COMPOSITIONS

The present invention relates to a method for inhibiting the growth of micro-organisms in a latex, especially a sterically stabilised or cationic stabilised latex and to compositions for use in the method.

Latices are a colloidal dispersion of a polymeric substance in a liquid medium which is usually aqueous and are used widely in many industrial applications such as paints, adhesives and sealants. However, latices are prone to attack by various micro-organisms which can result in an number of undesirable side effects including discolouration of the latex, destabilisation of the latex, loss of latex viscosity, the production of mal odours, the production of corrosive by-products resulting from the microbial metabolism and the generation of gases during storage. To minimise these problems anti-microbial agents are added to the latex to inhibit the growth of micro-organsims.

1,2-benzisothiazolin-3-one is used as a preservative in latices, particularly for the preservation of paints. This compound is commercially available from Avecia Limited as Proxel™.

Various isothiazolinone derivatives are also used in the preservation of latices, for example 2-methyl-4,5-trimethylene-4-isothiazolin-3-one and a blend of 5-chloro-2-methyl-4-isothiazolin-3-one and 2-methyl-4-isothiazolin-3-one (commercially available as Kathon™ from Rohm and Haas). Biocides are also added to latices to provide protection to the end use of the latex. For example, 2-n-octyl-4-isothiazolin-3-one (commercially available as Skane™ from Rohm & Haas) is used to inhibit the growth of mildew on paint films.

However, certain micro-organisms commonly found in latices, especially pseudomonad species are more tolerant of isothiazolinones and can therefore be more difficult to control.

We have surprisingly found that a combination of certain anti-microbial compounds provide improved efficacy when used to inhibit the growth of micro-organisms in a latex.

According to a first aspect of the present invention there is provided a method for inhibiting the growth of micro-organisms in a latex comprising adding to the latex:

(a) a polymeric biguanide; and (b) an isothiazolinone of the Formula (1) or a salt or complex thereof:

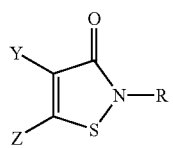

Formula (1)

wherein:

R is H, alkyl, cycloalkyl or aralkyl; and

Y and Z each independently are H, halogen, $C_{1-4}$-alkyl or Y and Z together with the carbon atoms to which they are attached form an optionally substituted 5 or 6 membered ring.

Isothiazolinone

When R is alkyl it may be linear or branched but is preferably linear. Preferred alkyl groups include $C_{1-8}$-alkyl, more preferably $C_{1-4}$-alkyl. Examples of preferred alkyl groups include for example methyl, ethyl, n-propyl, isopropyl, n-pentyl, n-butyl, isobutyl, tert-butyl and n-octyl.

When R is cycloalkyl, it is preferably cyclopropyl, cyclopentyl, or cyclohexyl.

When R is aralkyl, it preferably contains from 1 to 6, most preferably 1 or 2 carbon atoms in the alkylene group attaching the aryl group to the isothiazolinone ring. Preferred aralkyl groups include benzyl, 2-naphthylethyl and especially 2-phenylethyl.

When Y or Z is halogen it is preferably iodine, bromine and especially chlorine.

When Y and Z together with the carbon atoms to which they are attached form an optionally substituted 5 or 6 membered ring it is preferably an optionally substituted aryl (especially an optionally substituted benzene ring), an optionally substituted cyclopentene or an optionally substituted cyclohexene ring. Preferred optional substituents on the 5- or 6-membered ring are selected from hydroxy, halogen (especially chlorine), $C_{1-4}$-alkyl and $C_{1-4}$-alkoxy. It is preferred however that the ring is unsubstituted.

When Y and Z are H, halogen or $C_{1-4}$-alkyl, it is preferred that R is $C_{1-8}$-alkyl, $C_{3-5}$-cycloalkyl or aralkyl, more preferably $C_{1-8}$-alkyl and especially $C_{1-4}$-alkyl.

In an embodiment of the invention when R is n-octyl it is preferred that Y and Z are either both chlorine or both hydrogen. Such isothiazolinones are disclosed in U.S. Pat. No. 4,105,431.

Examples of suitable isothiazolinones include 5-chloro-2-methyl-4-isothiazolin-3-one, 2-methyl-4-isothiazolin-3-one, 4,5-dichloro-2-methylisothiazolin-3-one, 2-n-octyl-isothiazolin-3-one, 1,2-benzisothiazolin-3-one, 4,5-trimethylene-4-isothiazolin-3-one and 2-methyl-4,5-trimethylene-4-isothiazolin-3-one, 2-n-butyl-1,2-benzisothiazolin-3-one and mixtures comprising two or more of the foregoing compounds.

In a preferred embodiment of the present invention the isothiazolinone of Formula (1) is a benzisothiazolinone of the Formula (2) or a salt or complex thereof:

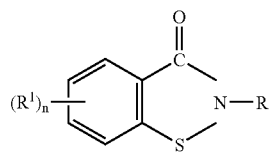

Formula (2)

wherein:

$R^1$ is hydroxy, halogen (especially chlorine), $C_{1-4}$-alkyl or $C_{1-4}$-alkoxy;

R is as hereinbefore defined; and n is from 0 to 4.

$R^1$, when present, is preferably located in one or both of the 5 and 6 positions of the phenyl ring of the benzisothiazolinone. However, it is particularly preferred that n is zero.

Preferred benzisothiazolinones of the Formula (2) are those in which R is H or $C_{1-5}$-alkyl, more preferably H or $C_{3-5}$-alkyl. Examples of compounds of the Formula (2) include, for example 1,2-benzisothiazolin-3-one, N-n-butyl-, N-methyl-, N-ethyl-, N-n-propyl-, N-isopropyl-, N-n-pentyl-, N-cyclopropyl-, N-isobutyl-, and N-tert-butyl-1,2- benzisothiazolin-3-one. It is especially preferred that the benzisothiazolinone of Formula (2) is 1,2-benzisothiazolin-3-one.

When R is H in Formula (1) or Formula (2) the isothiazolinone may be used in the form of a salt or complex thereof. The salt or complex may be with any suitable cation such as an amine (including an alkanolamine) or a metal. Preferred salts are those with a monovalent metal especially an alkali metal salt such as lithium, sodium or potassium. Most preferably, the alkali metal salt is a sodium salt.

Polymeric Biguanide

Preferably the polymeric biguanide comprises at least two biguanide units of Formula (3):

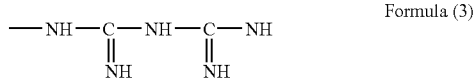

Formula (3)

linked by a bridging group which contains at least one methylene group. The bridging group preferably includes a polymethylene chain, optionally incorporating or substituted by one or more hetero atoms such as oxygen, sulphur or nitrogen. The bridging group may include one or more cyclic moieties which may be saturated or unsaturated. Preferably, the bridging group is such that there are at least three, and especially at least four, carbon atoms directly interposed between two adjacent biguanide units of Formula (3). Preferably, there are not greater than ten and especially not greater than eight carbon atoms interposed between two adjacent biguanide units of Formula (3).

The polymeric biguanide may be terminated by any suitable group, such as a hydrocarbyl, substituted hydrocarbyl or an amine group or a cyanoguanidine group of the formula:

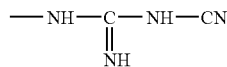

When the terminating group is hydrocarbyl, it is preferably alkyl, cycloalkyl, aryl or aralkyl. Preferred alkyl, cycloalkyl, aryl or aralkyl groups are as defined for R in Formula (1). Preferred aryl groups include phenyl groups. When the terminating group is substituted hydrocarbyl, the substituent may be any substituent that does not exhibit undesirable adverse effects on the microbiological properties of the polymeric biguanide. Examples of such substituents are aryloxy, alkoxy, acyl, acyloxy, halogen and nitrile.

When the polymeric biguanide contains two biguanide groups of Formula (3) the biguanide is a bisbiguanide. The two biguanide groups are preferably linked through a polymethylene group, especially a hexamethylene group.

The terminating groups in such bisbiguanides are preferably $C_{1-10}$-alkyl which may be linear or branched and optionally substituted aryl, especially optionally substituted phenyl. Examples of such terminating groups are 2-ethylhexyl and 4-chlorophenyl. Specific examples of such bisbiguanides are compounds represented by Formula (4) and (5) in the free base form:

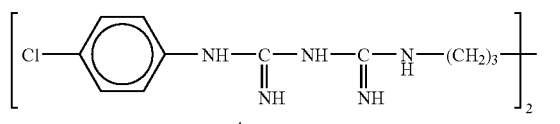

Formula (4)

and

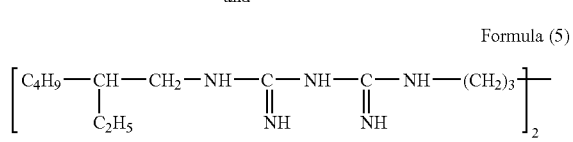

Formula (5)

The polymeric biguanide preferably contains more than two biguanide units of Formula (3) and is preferably a linear polymeric biguanide which has a recurring polymeric chain represented by Formula (6) or a salt thereof:

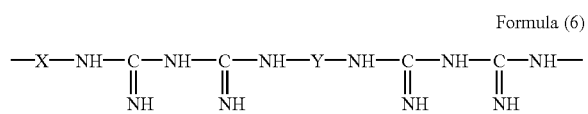

Formula (6)

wherein X and Y represent bridging groups which may be the same or different and in which together the total of the number of carbon atoms directly interposed between the pairs of nitrogen atoms linked by X plus the number of carbon atoms directly interposed between the pairs of nitrogen atoms linked by Y is more than 9 and less than 17.

The bridging groups X and Y preferably consists of polymethylene chains, optionally interrupted by hetero atoms, for example, oxygen, sulphur or nitrogen. X and Y may also incorporate moieties which may be saturated or unsaturated, in which case the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

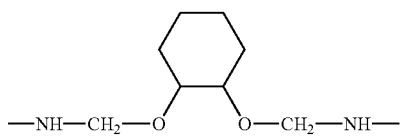

is 4 and not 8.

The linear polymeric biguanides having a recurring polymer unit of Formula (6) are typically obtained as mixtures of polymers in which the polymer chains are of different lengths. Preferably, the number of individual biguanide units of formulae:

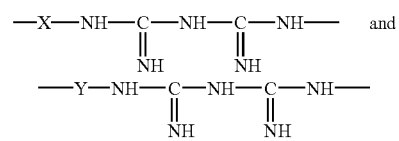

is, together, from 3 to about 80.

The preferred linear polymeric biguanide is a mixture of polymer chains in which X and Y are identical and the individual polymer chains, excluding the terminating groups, are of the Formula (7) or a salt thereof:

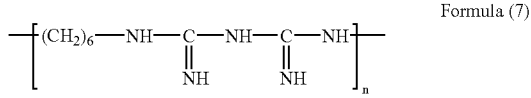

Formula (7)

wherein n is from 4 to 40 and especially from 4 to 15. It is especially preferred that the average value of n is about 12. Preferably, the average molecular weight of the polymer in the free base form is from 1100 to 3300.

The linear polymeric biguanides may be prepared by the reaction of a bisdicyandiamide having the formula:

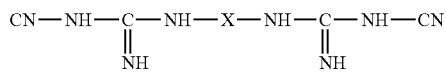

with a diamine $H_2N$—Y—$NH_2$, wherein X and Y have the meanings defined above, or, by reaction between a diamine salt or dicyanimide having the formula:

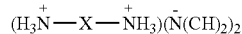

with a diamine $H_2N$—Y—$NH_2$ wherein X and Y have the meanings defined above. These methods of preparation are described in UK specifications numbers 702,268 and U.S. Pat. No. 1,152,243 respectively, and any of the polymeric biguanides described therein may be used in the present invention.

As noted hereinbefore, the polymer chains of the linear polymeric biguanides may be terminated either by an amino group or by a cyanoguanidine group:

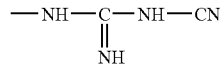

This cyanoguanidine group can hydrolyse during preparation of the linear polymeric biguanide yielding a guanidine end group. The terminating groups may be the same or different on each polymer chain.

A small proportion of a primary amine R—$NH_2$, where R represents an alkyl group containing from 1 to 18 carbon atoms, may be included with the diamine $H_2N$—Y—$NH_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used.

The polymeric biguanides readily form salts with both inorganic and organic acids. Preferred salts of the polymeric biguanide are water-soluble. When the polymeric biguanide is represented by a compound of Formula (4) in the free base form, a preferred water soluble salt is the digluconate. When the polymeric biguanide is represented by a compound of Formula (5) in the free base form, a preferred water soluble salt is the diacetate. When the polymeric biguanide is a mixture of linear polymers represented by Formula (7) in the free base form, the preferred salt is the hydrochloride.

It is especially preferred that the polymeric biguanide is a mixture of linear polymers, the individual polymer chains of which, excluding the terminating groups, are represented by Formula (7) in the hydrochloride salt form. This is commercially available from Avecia Ltd. under the trademark VANTOCIL™.

Latex

The present method is suitable for protecting a wide range of latices. The latex may be a natural latex, for example as produced by rubber trees, an artificial latex, prepared by dispersing polymer particles in a liquid medium or more preferably, a synthetic latex prepared by emulsion polymerisation of one or more monomers.

The polymer particles in the latex are usually stabilised in the liquid medium using ionic or steric forces to inhibit the flocculation/coagulation of the polymer particles in the liquid medium. When the latex is stabilised using ionic stabilisation the polymer particles are stabilised primarily by cationic or anionic groups associated with the surface of the polymer particles. The ionic groups may be present as an ionic surfactant/dispersant present in the liquid medium of the latex or as an ionic group which is an integral part of the polymer. Such ionic groups may be introduced into the polymer by using cationic or anionic monomers during the emulsion polymerisation process used to prepare the latex.

When the latex is stabilised using steric stabilisation the polymer particles are stabilised principally using steric hindrance provided by non-ionic surfactants/dispersants or water-soluble colloids.

When the latex is an anionic stabilised latex it is preferably stabilised using an anionic surfactant, or by anionic groups which form part of the polymer particle in the latex. Suitable anionic surfactants include alkylarylsulfonates (for example calcium dodecylbenzenesulfonate), alkylsulfates (for example sodium dodecylsulfate), sulfosuccinates (for example sodium dioctylsulfosuccinate), alkylethersulfates, alkylarylethersulfates, alkylether carboxylates, alkylarylethercarboxylates, lignin sulfonates or phosphate esters.

When the latex is stabilised by anionic groups present in the polymer of the latex the groups are preferably introduced by polymerising or more preferably co-polymerising anionic monomers during the emulsion polymerisation process used in the preparation of the latex. Suitable anionic monomers which may be used in the preparation of the latex include those which carry one or more sulpho or, more preferably carboxy groups or salts thereof. For example, an unsaturated mono or dicarboxylic acid. Suitable unsaturated mono carboxylic acids include acrylic acid or methacrylic acid. Suitable unsaturated dicarboxylic acids include itaconic acid, fumaric acid or maleic acid.

However, it is preferred that the latex is a cationic or sterically stabilised latex, because we have found that the presence of some anionic surfactants can result in the formation of undesirable precipitates when the isothiazolinone and polymeric biguanide are added to the latex. Accordingly it is preferred that the latex is substantially free from anionic compounds, especially anionic surfactants. Preferably the latex contains less than 5%, more preferably less than 1% and especially less than 0.05% by weight of anionic compounds, for example anionic surfactants such as alkyl sulphonate or alkyl carboxylates.

When the latex is a cationic stabilised latex it is preferably stabilised using a cationic surfactant, or by cationic groups which form part of the polymer particle in the latex.

Suitable cationic surfactants include aliphatic, mono-, di- and polyamines derived from fatty and rosin acids, especially those with one or more tertiary or quaternary ammonium groups. Preferably the fatty and rosin acids from which the surfactants are derived contain one or more $C_{10-24}$-alkyl or alkenyl groups more preferably $C_{12-24}$-alkyl or alkenyl groups more preferably a $C_{16-18}$-alkyl or alkenyl group. Suitable amine surfactants include diamines of the formula $R^2NH(CH_2)_mNH_2$ wherein m is 2 or 3 and $R^2$ is a mixed alkyl or alkenyl group derived from coconut, tallow or soyabean oil; alkylamine ethoxylates such as aliphatic amine ethoxylates, and fatty alkyl-1,3-propanediamine ethoxylates; ethylenediamine alkoxylates; 2-alkyl imidazolines and ethoxylated derivatives thereof; and alkoxylated allkanolamides. Suitable surfactants containing quaternary ammonium group(s) include for example di(hydrogenated tallow alkyl)-dimethyl quaternary ammonium chlorides such as Arquad™. 2HT-75 (Akzo Chemicals Inc., Chicago, Ill.); tallow alkyl benzyl dimethyl quaternary ammonium chloride such as Kemamine™ BQ-9742C (Witco Chemical Corp., Memphis, Tenn.); hydrogenated tallow alkyl benzyl dimethyl quaternary ammonium chloride such as Kemamine™ Q-9702C (Witco Chemical Corp.); methyl bis(soya alkyl amidoethyl)2-hydroxyethyl quaternary ammonium methyl sulfate such as Accosoft™ 750 (Stepan Co., Northfield, Ill.); methyl bis(tallow alkyl amidoethyl)2-hydroxyethyl quaternary ammonium methyl sulfate such as Accosoft™ 501 (Stepan Co.); fatty-alkyl trimethlammonium salts, for example tallow-alkyl trimethlammonium salts; fatty-alkylpyridinium salts for example cetylpyridinium chloride; and quaternary ammonium esters.

When the latex is stabilised by cationic groups present in the polymer of the latex the groups are preferably introduced by polymerising or more preferably co-polymerising cationic monomers during the emulsion polymerisation process used in the preparation of the latex. Preferred cationic monomers are those which carry one or more cationic group(s), especially vinyl, acrylate and (alkyl) acrylate (especially (meth)acrylate, (ethyl)acrylate and (propyl)acrylate) monomers which carry a cationic group.

Suitable cationic groups carried by the monomers include amines, preferably secondary or more preferably tertiary amines; nitrogen containing heterocyclic groups, for example pyridyl or pyrrolidone groups; and quaternary ammonium groups.

Examples of preferred cationic acrylate and (alkyl)acrylate monomers include 2-(dimethylaminoethyl) acrylate, 2-(dimethylaminoethyl) (meth)acrylate, 2-(dimethylaminoethyl) (ethyl)acrylate or 2-(dimethylaminoethyl) (propyl)acrylate and quaternary ammonium salts thereof, especially the dimethyl sulphate quaternary ammonium salt. Examples of preferred vinyl monomers carrying a cationic group include vinyl pyridine or vinyl pyrrolidone and salts thereof.

When the latex is sterically stabilised it is preferably stabilised using a non-ionic surfactant or dispersant or a water-soluble colloid. A wide range of non-ionic surfactants are suitable for stabilising the latex, the selection of which will depend upon the polymer in the latex and the end use of the latex. Suitable non-ionic surfactants include polyoxyethylene surfactants; alcohol ethoxylates; alkylphenolethoxylates; carboxylic acid esters, preferably those obtained by reaction of a fatty acid and a polyol; glycerol esters of fatty acids; polyoxyethylene esters obtainable from the reaction of a fatty acid with a polyethylene glycol; carboxylic amides especially those obtainable by the condensation of fatty acids with a hydroxyalkylamine or a diethanolamine; ethoxylated fatty acid amides; polyalkyleneoxide block copolymers, especially poly(oxyethylene-co-oxypropylene) surfactants.

Suitable water-soluble colloids which may be used to stabilise the latex are water-soluble long chain polymers, for example a poly(vinylacetate) and partially hydrolysed derivatives thereof; polyvinylalcohols; starches, hydroxethylcellulose and glycol ether derivatives thereof; and hydroxymethyl cellulose and glycol ether derivatives thereof.

It is especially preferred that the latex is stabilised with a partially hydrolysed poly(vinylacetate) or a poly(vinylalcohol). Suitable examples are those available from Hoechst Aktingesellschaft under the trade name Mowiol™ 8-88 and Mowiol™ 18-88 but are not limited thereto.

As hereinbefore mentioned the method according to the present invention may be used to protect a wide range of latices. The polymer particles present in the latex will be dependent upon the end application of the latex. Suitable latices include, but are not limited to those obtainable by the polymerisation or emulsion polymerisation of one or more acrylates and (alkyl)acrylates (especially alkylacrylates and alkyl(meth)acrylates); optionally substituted styrenes; methacrylamides; allyl compounds; vinyl ethers; vinyl ketones; vinyl esters; vinyl halides; olefins; unsaturated nitriles and mixtures comprising two or more of the foregoing.

Examples of suitable alkyl acrylates and alkyl(meth) acrylates include methyl acrylate, ethyl acrylate, n-propyl acrylate, isopropyl acrylate, n-butyl acrylate, isobutyl, sec-butyl acrylate, amyl acrylate, hexyl acrylate, 2-ethylhexyl acrylate, octyl acrylate, tert-octyl acrylate, 2-phenoxyethyl acrylate, di- and tripropylene glycol diacrylate, 2-chloroethyl acrylate, 2-bromoethyl acrylate, 4-chlorobutyl acrylate, cyanoethyl acrylate, 2-acetoxyethyl acrylate, dimethylaminoethyl acrylate, benzyl acrylate, methoxybenzyl acrylate, 2-chlorocyclohexyl acrylate, cyclohexyl acylate, furfuryl acrylate, tetrahydrofurfuryl acrylate, hydroxyethyl(meth) acrylate, hydroxypropyl(meth) acrylate, 5-hydroxypentyl acrylate, 2,2-dimethyl-3-hydoxypropyl acrylate, 2-methoxyethyl acrylate, 3-methoxybutyl acrylate, 2-ethoxyethyl acrylate, 2-iso-propoxyethyl acrylate, 2-butyoxyethyl acrylate, 2-(2-methoxyethoxy)ethyl acrylate, 2-(2-butoxyethoxy)ethyl acrylate, 1-bromo-2-methoxyethyl acrylate, 1,1-dichloro-2-ethoxyethyl acrylate, methyl methacrylate, ethyl methacrylate, n-propyl methacrylate, isopropyl methacrylate, n-butyl methacrylate, isobutyl methacrylate, sec-butyl methacrylate, amyl methacrylate, hexyl methacrylate, cyclohexyl methacrylate, benzylmethacrylate, chlorobenzyl methacrylate, octyl methacrylate, N-ethyl-N-phenylaminoethyl methacrylate, 2-(3-phenylpropyloxy)ethyl methacrylate, dimethylaminophenoxyethyl methacrylate and furfuryl methacrylate.

Suitable optionally substituted styrenes include styrene, divinyl benzene, methylstyrene, dimethylstyrene, trimethylstyrene, ethylstyrene, diethylstyrene, isopropylstyrene, butylstyrene, hexylstyrene, cyclohexylstyrene, decylstyrene, chloromethylstyrene, trifluoromethylstyrene, ethoxymethylstyrene, acetoxymethylstyrene, methoxystyrene, 4-methoxy-3-methylstyrene, dimethoxystyrene, chlorostyrene, dichlorostyrene, trichlorostyrene, tetrachlorostyrene, pentachlorostyrene, bromostyrene, dibromostyrene, iodostyrene, trifluorostyrene and 2-bromo-4-trifluoromethylstyrene.

Suitable methacrylamides include those containing less than 12 carbon atoms. Examples include methylmethacrylamide, tert-butylmethacrylamide, tert-octylmethacrylamide, benzylmethacrylamide, cyclohexylmethacrylamide, phenylmethacrylamide, dimethylmethacrylamide, dipropylmethacrylamide, hydroxyethyl-N-methylmethacrylamide, N-methylphenylmethacrylamide, N-ethyl-N-phenylmethacrylamide and methacrylhydrazine.

Suitable allyl compounds include allyl acetate, allyl caproate, allyl caprylate, allyl laurate, allyl palmitate, allyl stearate, allyl benzoate, allyl acetoacetate, allyl lactate, allyloxyethanol, allyl butyl ether and allyl phenyl ether.

Suitable vinyl ethers include those containing less than 20 carbon atoms. Examples include methyl vinyl ether, butyl vinyl ether, hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether and dimethylaminoethyl vinyl ether.

Suitable vinyl ketones include those containing less than 12 carbon atoms. Examples include methyl vinyl ketone, phenyl vinyl ketone and methoxyethyl vinyl ketone.

Suitable vinyl esters include vinylacetate.

Suitable vinyl halides include vinyl chloride, vinylidene chloride and chlorotrifluoro ethylene.

Suitable olefins include unsaturated hydrocarbons having less than 20 carbon atoms. Examples include dicyclopentadiene, propylene, 1-butene, 1-pentene, 1-hexene, 4-methyl-1-pentene, 1-heptene, 1-octene, 1-decene, 5-methyl-1-nonene, 5,5-dimethyl-1-octene, 4-methyl-1-hexene, 4,4-dimethyl-1-pentene, 5-methyl-1-hexene, 4-methyl-1-heptene, 5-methyl-1-heptene, 4,4-dimethyl-1-hexene, 5,5,6-trimethyl-1-heptene, 1-dodecene and 1-octadecene and especially ethylene.

Suitable unsaturated nitriles include acrylonitrile and methacrylonitrile.

Further components may be added to the monomer(s) during the preparation of the latex to modify the properties of the polymer particles, for example plasticisers and stabilizers. The plasticiser or stabiliser may be any of those commonly used in the latices fabrication industry and is preferably a liquid. Examples of suitable plasticisers or stabilisers are esters of aromatic and aliphatic mono- and di-carboxylic acids and linear or branched alcohols especially $C_{8-10}$-alcohols; epoxidised fatty acid esters and epoxidised vegetable oils. Specific examples of plasticisers are di-hexyl-, di-octyl-, di-nonyl, di-isodecyl-, and di-(2-ethylhexyl)-adipates; sebacates, trimellitates and phthalates; epoxidised octyl stearate, epoxidised soya bean oil and phosphate esters of formula O=P $(OR^3)_3$ wherein $R^3$ is hydrocarbyl, particularly phenyl and especially $C_{1-4}$-alkyl and low molecular weight oligo- and poly-esters such as those obtainable by reacting 1,3-butanediol with adipic acid.

The pH of the latex is preferably from 3 to 10.

The present method is particularly effective for inhibiting the growth of micro-organisms in latices used in paints, adhesives and sealants. Examples of such latices include those obtainable by the polymerisation or emulsion co-polymerisation of for example, of one or more acrylates and (alkyl)acrylates (especially alkylacrylates and alkyl(meth) acrylates); optionally substituted styrenes; methacrylamides; allyl compounds; vinyl ethers; vinyl ketones; vinyl esters; vinyl halides; olefins; unsaturated nitriles and mixtures comprising two or more of the foregoing, especially latices obtainable by the polymerisation or emulsion co-polymerisation of the following monomers; methyl methacrylate, vinyl acetate, methyl acrylate, ethyl acrylate, butyl acrylate, n-hexyl acrylate, n-octyl acrylate, styrene, 2-ethylhexyl acrylate, acrylic acid, acrylonitrile, ethylene, vinyl acetate, vinyl chloride and ethylene; and especially latices obtainable by the polymerisation or emulsion co-polymerisation of methyl methacrylate with butylacrylate, 2-ethylhexyl acrylate or ethyl acrylate.

In an especially preferred embodiment the latex is stabilised by a water-soluble colloid such as a partially hydrolysed poly(vinylacetate) or a poly(vinylalcohol), and the latex is one of:
(i) a latex obtainable by emulsion co-polymerisation of methyl methacrylate with butylacrylate, 2-ethylhexyl acrylate or ethyl acrylate;
(ii) a polyvinylacetate latex; and
(iii) a latex obtainable by emulsion polymerisation of vinyl acetate and ethylene.

In this especially preferred embodiment the water soluble colloid is preferably a poly(vinylalcohol) such as a Mowiol™ 8-88 and Mowiol™ 8-18 but is not limited thereto.

The liquid medium in which the polymer particles are dispersed is preferably water or a mixture of water and one or more water-miscible organic solvent(s). Examples of suitable water-miscible organic solvents are acetic acid, N,N-dimethylformamide, glycols such as ethylene glycol, propylene glycol, dipropylene glycol; methanol, ethanol, dimethylsulphoxide, N-methyl-2-pyrrolidone and lower $C_{1-4}$-alkyl carbitols such as methyl carbitol. Preferred water-miscible organic solvents are glycols with 2 to 6 carbon atoms, poly-alkylene glycols with 4 to 9 carbon atoms or mono $C_{1-4}$-alkyl ethers of glycols with 3 to 13 carbon atoms. The most preferred water-miscible organic solvent is propylene glycol.

The latex may contain other additives, for example viscosity control agents, anti-foam additives, pH modifiers, traces of the initiators and monomers used in the preparation of the latex, colorants and fillers such as clays, calcium carbonate and calcium sulphates.

The polymeric biguanide and the isothiazolinone may be added to the latex sequentially in any order, or simultaneously, to give a concentration in the latex which is effective to control or eliminate the growth of micro-organisms in the latex. The amount of polymeric biguanide and isothiazolinone of Formula (1) added to the latex will be dependent upon the nature of the latex, the conditions under which it will be stored and the particular isothiazolinone and polymeric biguanide selected.

Preferably sufficient polymeric biguanide is added to the latex to give a concentration therein of from 10 to 1000 ppm by weight of the polymeric biguanide relative to the total weight of the latex.

When an isothiazolinone in which Y and Z in Formula (1) are H, halogen or $C_{1-4}$-alkyl is employed, it is preferred that sufficient isothiazolinone is added to the latex to give a concentration therein of from 0.5 to 100 ppm, more preferably from 1 to 50 ppm and especially from 5 to 25 ppm by weight relative to the total weight of the latex.

When an isothiazolinone in which Y and Z in Formula (1) together with the carbon atoms to which they are attached form an optionally substituted 5 or 6 membered ring, especially a benzene ring, is employed, it is preferred that sufficient isothiazolinone is added to the latex to give a concentration therein of from 1 to 500 ppm, more preferably from 5 to 200 ppm by weight relative to the total weight of the latex.

When the polymeric biguanide and isothiazolinone are added to the latex simultaneously it is preferred that they are added in the form of a composition comprising the isothiazolinone, the polymeric biguanide and optionally a medium.

The medium, when present, is preferably a liquid medium, more preferably water, a mixture of water and one or more organic solvents or an organic solvent. Examples of organic solvents that may be employed include include $C_{1-6}$-alkanols (especially $C_{1-4}$-alkanols), for example methanol, ethanol, n-propanol, isopropanol, n-butanol, sec-butanol, tert-butanol, n-pentanol, cyclopentanol and cyclohexanol; linear amides, preferably dimethylformamide or dimethylacetamide; alkanolamides, for example lactamide, lactamidopropyltrimethylammonium chloride, acetamide and acetamidomonoethanolamine; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, 1,3-butylene glycol, pentylene glycol, hexylene glycol and thiodiglycol and oligo- and poly-alkyleneglycols, preferably diethylene glycol, triethylene glycol, polyethylene glycol, dipropylene glycol, tripropylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol, propyleneglycol butyl ether and 1-propoxy-2-propanol. It is especially preferred that the medium is water or a mixture of water and one or more water-miscible organic solvents. Examples of suitable water-miscible organic solvents are acetic acid, N,N-dimethylformamide, glycols such as ethylene glycol, propylene glycol, dipropylene glycol; methanol, ethanol, dimethylsulphoxide, N-methyl-2-pyrrolidone and lower $C_{1-4}$-alkyl carbitols such as methyl carbitol. Preferred water-miscible organic solvents are glycols with 2 to 6 carbon atoms, poly-alkylene glycols with 4 to 9 carbon atoms or mono $C_{1-4}$-alkyl ethers of glycols with 3 to 13 carbon atoms. The most preferred water-miscible organic solvent is propylene glycol. The polymeric biguanide and isothiazolinone may be dissolved in the medium to provide a solution therein. Alternatively one or both may be present in the medium as an emulsion or dispersion.

Latices treated with a polymeric biguanide and an isothiazolinone of Formula (1) according to the present method exhibit long term stability against spoilage by micro-organisms such as fungi, algae, yeasts and especially bacteria.

According to a further aspect of the present invention there is provided a composition comprising a latex, a polymeric biguanide and an isothiazolinone of the Formula (1). The preferred polymeric biguanide and isothiazolinone are as hereinbefore described with reference to the first aspect of the invention.

In a preferred embodiment the composition comprises a steric or cationic stabilised acrylic latex; a linear polymeric biguanide which is a mixture of polymer chains in which the individual polymer chains, excluding the terminating groups, are of the Formula (7) or a salt thereof as hereinbefore described; and a benzisothiazolinone derivative of the hereinbefore described Formula (2) or a salt or complex thereof.

We have found that the combination of the polymeric biguanide and isothiazolinone used in the present method exhibits a synergistic effect against the micro-organisms commonly found in latices, especially against fungi such as *Aspergillus Niger*, yeasts such as *Candida albicans* and bacteria, especially gram-negative bacteria such as *Pseudomonas aeruginosa*. Compositions comprising the polymeric biguanide and isothiazolinone used in the method according to the present invention exhibit a sum of the Fractional Inhibitory Concentration (hereinafter FIC) for each component which is below 1. Preferably, the sum of the FIC values is not greater than 0.8, more preferably not greater than 0.7 and especially not greater than 0.5. The FIC is the ratio of the amount of each component in the composition relative to its Minimum Inhibitory Concentration (MIC) when used alone. Thus, when the sum of the FIC values is one, the two components exhibit a mere additive effect. When the sum of the FIC values is below one, the mixture is synergistic. When the sum of the FIC values is between one and two the two components are considered to be independent. When the sum of the FIC values is greater than two, the mixture is antagonistic. The FIC values are preferably determined by constructing an isobologram wherein each component in a matrix array is varied stepwise from a concentration in excess of the MIC down to zero ppm. The isobologram therefore allows the smallest value of the sum of the FIC's for each component in the composition to be determined and hence the optimal concentration for each component in the composition.

Certain compositions used in the method according to the present invention are novel.

According to a further aspect of the present invention there is provided an anti-microbial composition comprising:
(i) a linear polymeric biguanide which is a mixture of polymer chains in which the individual polymer chains, excluding the terminating groups, are of the Formula (7) or a salt thereof as hereinbefore described; and
(ii) a benzisothiazolinone derivative of the hereinbefore described Formula (2) or a salt or complex thereof as hereinbefore described.

Preferred benzisothiazolinone derivatives of Formula (2) are as hereinbefore described with reference to the first aspect of the invention. It is especially preferred that component (ii) is 1,2-benzisothiazolinone.

The weight ratio of the linear polymeric biguanide:benzisothiazolinone in the anti-microbial composition may vary over wide limits for example from 99:1 to 1:99, more preferably from 10:1 to 1:10. It is especially preferred that the weight ratio of component (i) and component (ii) is close to the lowest sum of the FIC values for each of the components as determined from an isobologram as hereinbefore described. It is especially preferred that the weight ratio of the linear polymeric biguanide benzisothiazolinone in the antimicrobial composition is from 4:1 to 1:4.

As hereinbefore described the antimicrobial compositions according to this aspect of the invention are useful for inhibiting the growth of microorganisms in latices. The antimicrobial compositions are also useful for inhibiting the growth of microorganisms in or on a wide range of other media, especially industrial media. Examples of industrial media include cooling water liquors, paper mill liquors, metal working fluids, geological drilling lubricants, polymer emulsions, surface coating compositions (especially varnishes and lacquers) and solid materials, especially wood, plastics materials and leather. The amount of the anti-microbial composition according to this aspect of the invention required to protect such media will be dependant upon the medium to be protected and the conditions to which it will be exposed. Appropriate concentrations of the anti-microbial composition can be readily determined by those skilled in the art by simple experimental trials.

The anti-microbial composition may be added to the medium directly, however, for ease of handling and dosing, it is generally convenient to formulate the anti-microbial composition as a formulation comprising an anti-microbial composition according to the present invention and a carrier.

The carrier may be a solid but is preferably a liquid and the formulation is preferably a solution, suspension or emulsion of the antimicrobial composition in the liquid.

The carrier is generally selected so that the antimicrobial composition is compatible with the medium to be protected. Thus, for example, if the medium to be protected is a solvent-based paint, lacquer or varnish the carrier is preferably a solvent, especially a non-polar solvent such as white spirits (HSCN number 27100021). If the medium to be protected is a plastics material, the carrier is preferably a plasticiser typically used in the fabrication of plastic articles such as dioctylphthalate or epoxidised soya bean oil. If the medium to be protected is an aqueous medium, the carrier is preferably water or a water-miscible organic solvent or mixture thereof. Examples of suitable water-miscible organic solvents are acetic acid, N,N-dimethylformamide, glycols such as ethylene glycol, propylene glycol, dipropylene glycol; methanol, ethanol, dimethylsulphoxide, N-methyl-2-pyrrolidone and lower $C_{1-4}$-alkyl carbitols such as methyl carbitol. Preferred water-miscible organic solvents are glycols with 2 to 6 carbon atoms, poly-alkylene glycols with 4 to 9 carbon atoms or mono $C_{1-4}$-alkyl ethers of glycols with 3 to 13 carbon atoms. The most preferred water-miscible organic solvent is propylene glycol.

If the formulation is in the form of a suspension or emulsion, it preferably also contains a surface active agent to produce a stable dispersion or to maintain the non-continuous phase uniformly distributed throughout the continuous phase. Any surface active agent which does not adversely affect the biocidal activity of the compounds comprising the anti-microbial composition may be used. Preferred surface active agents are the preferred non-ionic or cationic surfactants and/or dispersants as hereinbefore described in relation to the first aspect of the invention, for example alkylene oxide adducts of fatty alcohols, alkyl phenols and amines such as ethylene diamine.

The invention is further illustrated by the following examples in which all parts are by weight unless otherwise stated and by the accompanying drawings wherein FIGS. 1–7 are isobolograms showing the anti-microbial activity of compositions according to the invention.

EXAMPLE 1

Investigation of Synergy Between Polyhexamethylene Biguanide (PHMB) and 1,2-Benzisothiazolin-3-one (BIT) against *Pseudomonas aeruginosa*

Bacteria

*Pseudomonas aeruginosa* NCIB 10421

Method

Maintenance of Stock Cultures

Bacteria were maintained on nutrient agar and fungi on malt agar or a spore suspension in physiological saline (0.85% w/v NaCl).

Calculation of Minimum Inhibitory Concentrations Against Mono-cultures

Bacteria were grown to stationary phase (18 h) in nutrient broth (approximately $10^9$ organisms per ml). A 0.1% (v/v) inoculum was used to seed fresh medium and 100 µl of the inoculum was then added to each well of a microtitre plate, except for the first well which contained 200 µl.

Using doubling dilutions, the concentration of the compounds under investigation were varied in each well along the ordinate axis. The presence or absence of growth was recorded by visual inspection after 24 hours incubation at 37° C.

Calculation of Antimicrobial Activity Against Mono-Cultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

The mixture (100 µl) was added to the plate so that the total volume in each well was 200 µl. Nutrient broth was used for *Ps.aeruginosa*. Plates were incubated for 16–24 hours at 37°. The presence or absence of growth was determined by visual inspection.

Results

TABLE 1

Antimicrobial Activity of Compounds Under Investigation
Table 1

| COMPOUND | MIC (ppm) against *Ps. aeruginosaa* |
|---|---|
| BIT | 32 |
| Vantocil$^{RTM}$ IB | 32 |

Vantocil$^{RTM}$ IB - is a 20% solution of polyhexamethylene biguanide (PHMB) hydrochloride available from Avecia Limited.
BIT is 1,2-benzisothiazolin-3-one available from Avecia Limited as PROXEL$^{RTM}$ GXL.

Calculation of Synergy Against Mono-Cultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. Fractional Inhibitory Concentrations are the concentration of biocide which controlled growth in the mixture divided by the MIC of that biocide. FIC values for both compounds in the mixture were calculated and the results are shown in Table 2. The sum of these two figures gives an indication of the action of the two biocides. A value less than one indicates a synergistic effect, if the total is unity or greater the action is additive and if the value is greater than two the biocides are antagonistic. If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, synergistic combinations give concave isoboles and antagonistic combinations give convex isoboles.

TABLE 2

Fractional Inhibitory Concentrations for BIT and Vantocil^RTM IB (PHMB) against *Ps. aeruginosa*

Table 2

| COMPOUND | FIC VALUES | | | | | | | |
|---|---|---|---|---|---|---|---|---|
| Vantocil^RTM IB | 1 | 0.43 | 0.29 | 0.14 | 0.14 | 0.14 | 0.14 | 0.00 |
| BIT | 0 | 0.14 | 0.29 | 0.43 | 0.57 | 0.71 | 0.86 | 1.00 |
| Total | 1 | 0.57 | 0.58 | 0.56 | 0.71 | 0.85 | 1.00 | 1.00 |

The activity of mixtures of butyl BIT and Vantocil^RTM IB (PHMB) against *Ps. aeruginosa* is shown in the isobologram comprising FIG. 1.
Vantocil^RTM IB - is a 20% solution of PHMB hydrochloride available Avecia Limited.
BIT - is 1,2-benzisothiazolin-3-one available from Avecia Limited as PROXEL^RTM GXL.

EXAMPLE 2

Investigation of Synergy Between Polyhexamethylene Biguanide (PHMB) and 2n-Butyl-1,2-benzisothiazolin-3-one (BBIT) against *Pseudomonas aeruginosa*

Bacteria

*Pseudomonas aeruginosa* NCIB 10421

Method

Maintenance of Stock Cultures

Bacteria were maintained on nutrient agar and fungi on malt agar or a spore suspension in physiological saline (0.85% w/v NaCl).

Calculation of Minimum Inhibitory Concentrations Against Monocultures

Bacteria were grown to stationary phase (18 h) in nutrient broth (approximately $10^9$ organisms per ml). A 0.1% (v/v) inoculum was used to seed fresh medium and 100 μl of the inoculum was then added to each well of a microtitre plate, except for the first well which contained 200 μl.

Using doubling dilutions, the concentration of the compounds under investigation were varied in each well along the ordinate axis. The presence or absence of growth was recorded by visual inspection after 24 hours incubation at 37° C.

Calculation of Antimicrobial Activity Against Monocultures

Microtitre plates were used for this assay. A simple matrix was constructed with varied concentrations of the two compounds from 2×MIC (minimum inhibitory concentration) down to zero concentration in a 10×10 array. As the microtitre plate has only 96 wells, the combinations of the two compounds that made up the extreme concentrations (highest and lowest) were omitted. Solutions were made up in broth at two times the final concentrations after pre-dissolving the compounds in distilled water.

Each mixture (100 μl) was added to the plate so that the total volume in each well was 200 μl. Nutrient broth was used for *Ps.aeruginosa*. Plates were incubated for 16–24 hours at 37° C. The presence or absence of growth was determined by visual inspection.

Results

TABLE 3

Antimicrobial Activity of Compounds Under Investigation

Table 3

| COMPOUND | MIC (ppm) against *Ps. aeruginosa* |
|---|---|
| Butyl BIT | 125 |
| Vantocil^RTM IB | 16 |

Vantocil^RTM IB - is a 20% solution of PHMB hydrochloride available from Avecia Limited.

Butyl BIT - is a 98% solution of 2n-butyl-1,2-benzisothiazolin-3-one (BBIT) available from Avecia Limited as Densil^RTM DN.

Calculation of Synergy Against Monocultures

The Minimum Inhibitory Concentration (MIC) is the lowest concentration of biocide which showed growth inhibition when used alone. For the purpose of Fractional Inhibitory Concentration (FIC) calculations, if a single biocide did not control growth, the MIC was taken as the highest concentration used. Fractional Inhibitory Concentrations are the concentration of biocide which controlled growth in the mixture divided by the MIC of that biocide. FIC values for both compounds in the mixture were calculated and the results are shown in Table 4. The sum of these two figures gives an indication of the action of the two biocides. A value less than one indicates a synergistic effect, if the total is unity or greater the action is additive and if the value is greater than two the biocides are antagonistic. If a graph with the axes representing the biocide Fractional Inhibitory Concentrations for the two biocides on linear scales is constructed, when the combination is additive the isobole (i.e. the line joining the points that represent all combinations with the same effect including the equally effective concentrations of the biocides used alone) is straight, synergistic combinations give concave isoboles and antagonistic combinations give convex isoboles.

TABLE 4

Fractional Inhibitory Concentrations for Butyl BIT and Vantocil^RTM IB (PHMB) against *Ps. aeruginosa*

Table 4

| COMPOUND | FIC VALUES | | | | |
|---|---|---|---|---|---|
| Butyl BIT | 0 | 0.12 | 0.24 | 0.37 | 1 |
| Vantocil^RTM IB | 1 | 0.37 | 0.25 | 0.12 | 0 |
| Total | 1 | 0.49 | 0.49 | 0.49 | 1 |

The activity of mixtures of butyl BIT and Vantocil^RTM IB (PHMB) against *Ps. aeruginosa* is shown in the isobologram comprising FIG. 2.

Vantocil^RTM IB - is a 20% solution of PHMB hydrochloride available Avecia Limited.

BIT - is a 98% solution of 2n-butyl-1,2-benzisothiazolin-3-one available from Avecia Limited as Densil^RTM DN.

EXAMPLE 3

Investigation of Synergy between Polyhexamethylene biguanide (PHMB) and N-Butyl Benzisothiazolin-3-one (Butyl BIT) against *Aspergillus Niger*. Fungus

*Aspergillus Niger* IMI 17454

METHOD

Maintenance of Stock Cultures

The fungus was maintained on malt agar.

Calculation of Minimum Concentrations (MICs) Against Monocultures

The MICs were calculated as described previously in examples 1 and 2.

Calculation of Antimicrobial Activity Against Monocultures

The antimicrobial activity was calculated as described previously in examples 1 and 2.

Results

TABLE 5

Antimicrobial Activity of Compounds Under Investigation

| COMPOUND | MIC (ppm) against *Aspergillus Niger* |
|---|---|
| Butyl BIT | 8 |
| Vantocil$^{RTM}$ IB | 16 |

Vantocil$^{RTM}$ IB - is a 20% solution of PHMB hydrochloride available from Avecia Limited.
Butyl BIT - is a 98% solution of 2n-butyl-1,2-benzisothiazolin-3-one (BBIT) available from Avecia Limited as Densil$^{RTM}$ DN.

Calculation of Synergy Against Monocultures

The synergy against monocultures was calculated as previously described in examples 1 and 2.

The activity of mixtures of n-butyl BIT and Vantocil® IM (PHMB) is shown in the isobologram constituting FIG. 3.

In the following examples 4 to 7, the antimicrobial activity of the compounds under investigation were tested in the presence of a latex stabilising, agent vinyl acetate ethylene copolymer (VAE).

EXAMPLE 4

Investigation of Synergy between Polyhexamethylene biguanide (PHMB) Hydrochloride and CMIT/MIT in VAE against *Acetobacter*

PHMB—is Polyhexamethylene biguanide (PHMB) hydrochloride available from Avecia Limited as Vantocil® IB.

CMIT/MIT—is a 1.5% solution of a 3:1 mixture of 5-chloro-2-methyl-4-isothiazolin-3-one and 2-methyl-4-isothiazolin-3-one available from Rohm and Haas as Kathon™ LX1.5.

VAE—is commercially available vinyl acetate ethylene copolymer.

Bacteria

An isolate of *Acetobacter*.

Method

Maintenance of Stock Cultures

The isolate of *Acetobacter* was grown on potato-dextrose agar (PDA) plates.

The following method was repeated for examples 4 to 7 as follows:

VAE (30 g) was weighed into sterile bottles and dosed with the two biocides under investigation. The samples were then inoculated with a suspension of bacteria (5% w/w) prepared from an agar lawn and incubated at 30° C. The bacterial growth was assessed by streaking on plates. (PDA for *Acetobacter*). The samples were judged to be free from viable bacteria if the plates were free from bacterial colonies following incubation at 30° C. for 120 hours. The samples were re-inoculated with fresh bacteria (5% w/w) every seven days.

Results

Calculation of Synergy Against Monocultures

Synergy against monocultures was calculates as previously described.

TABLE 7

Fractional Inhibitory Concentrations for Vantocil$^{RTM}$ IB (PHMB) and CMIT/MIT in VAE Against Acetobacter
Table 7

| COMPOUND | FIC Values | | | |
|---|---|---|---|---|
| CMIT/MIT | 0 | 0.33 | 0.67 | 1 |
| Vantocil$^{RTM}$ IB | 1 | 0.5 | 0.13 | 0 |
| Total | 1 | 0.85 | 0.80 | 1 |

CMIT/MIT - is a 1.5% solution of a 3:1 mixture of 5-chloro-2-methyl-4-isothiazolin-3-one and 2-methyl-4-isothiazolin-3-one available from Rohm and Haas as Kathon™ LX1.5.

The activity of mixtures of Vantocil® IB (PHMB) and CMIT/MIT in VAE aainst *acetobacter* is shown in FIG. 4.

EXAMPLE 5

Investigation of Synergy between Polyhexamethylene biguanide (PHMB) Hydrochloride and 2-Methyl-4-isothiazolin-3-one (MIT) in VAE (Vinyl Acetate Ethylene Copolymer (VAE)) Against *Acetobacter*

MIT—is 2-methyl-4-isothiazolin-3-one available from Rohm and Haas as Kordek™ 50.

Method

Example 5 was repeated in exactly the same way as example 4.

Results

TABLE 8

Fractional Inhibitory Concentrations for MIT and Vantocil$^{RTM}$ IB (PHMB) in VAE Against Acetobacter
Table 8

| COMPOUND | FIC Values | | | |
|---|---|---|---|---|
| MIT | 0 | 0.33 | 0.67 | 1 |
| Vantocil$^{RTM}$ IB | 1 | 0.50 | 0.13 | 0 |
| Total | 1 | 0.83 | 0.80 | 1 |

Vantocil$^{RTM}$ IB - is a 20% solution of polyhexamethylene biguanide (PHMB) hydrochloride available from Avecia Limited.

The isobologram of FIG. 5 shows the activity of a mixture of Vantocil® IB (PHMB) and MIT in VAE against *acetobacter*.

EXAMPLE 6

Investigation of Synergy between Polyhexamethylene biguanide (PHMB) Hydrochloride (Vantocil® IB) and 1,2-Benzisothiazolin-3-one (BIT) in VAE Against *Acetobacter*

Method

Example 6 was repeated in exactly the same way as examples 4 and 5.

Results

TABLE 9

Fractional inhibitory concentration for BIT and PHMB (Vantocil$^{RTM}$ IB) in VAE against Acetobacter
Table 9

| COMPOUND | | FIC Values | | |
|---|---|---|---|---|
| BIT | 0 | 0.33 | 0.67 | 1 |
| PHMB Vantocil$^{RTM}$ IB | 1 | 0.50 | 0.13 | 0 |
| Total | 1 | 0.83 | 0.80 | 1 |

The isobologram of FIG. 6 shows the activity of the mixtures of Vantocil® IB PHMB) and BIT in VAE against acetobacter.

EXAMPLE 7

Investigation of Synergy between Polyhexamethylene biguanide (PHMB) Hydrochloride (Vantocil® IB) and 2N-Butyl-1,2-Benzisothiazolin-3-one (Butyl BIT) in VAE Against *Acetobacter*

Butyl BIT—is a 98% solution of 2n-butyl-1,2-benzisothiazolin-3-one (BBIT) available from Avecia Limited as Densil® DN.

Vantocil® IB—is a 20% solution of polyhexamethylene biguanide (PHMB) hydrochloride available from Avecia Limited.

Method

Example 7 was repeated in exactly the same way as examples 4 to 6.

Results

TABLE 10

Fractional inhibitory concentrations for PHMB (Vantocil$^{RTM}$ IB) and Butyl BIT in VAE against Acetobacter
Table 10

| COMPOUND | | FIC Values | | |
|---|---|---|---|---|
| Butyl BIT | 0 | 0.20 | 0.40 | 1 |
| PHMB (Vantocil$^{RTM}$ IB) | 1 | 0.67 | 0.33 | 0 |
| Total | 1 | 0.87 | 0.73 | 1 |

The activity of this mixture of Vantocil® IB (PHMB) and butyl BIT in VAE against *acetobacter* is shown in the isobologram of FIG. 7.

EXAMPLE 8

Suitable formulations for use in inhibiting the growth of micro-organisms is a latex according to the present invention but not limited thereto were prepared as follows.

EXAMPLE 8a

Polyhexamethylene biguanide (PHMB) (Vantocil® IB) and 2N-Butyl-1,2-Benzisothiazolin-3-one (BBIT) Formulation

| Components | Weight % | Order of addition |
|---|---|---|
| Vantocil$^{RTM}$ IB is a 20% solution of Polyhexamethylene biguanide hydrochloride available from Avecia Limited. | 84.2 | 1 |
| Makon ™ 8 (Is ethoxylated nonyl phenol, available from Stepan Company) | 10.5 | 2 |
| Densil$^{RTM}$ DN is a 98% solution of 2n-Butyl-1,2-Benzisothiazolin-3-one available from Avecia Limited. | 5.3 | 3 |

Procedure:

Makon ™ 8 was added to Vantocil$^{RTM}$ IB with stirring. Densil$^{RTM}$ DN was then added slowly to achieve a clear light brown solution

EXAMPLE 8b

Polyhexamethylene biguanide (PHMB) (Vantocil® IB) and 1,2-Benzisothiazolin-3-one (BIT) Formulation

| Components | Weight % | Order of addition |
|---|---|---|
| Mixture 1 | | |
| Cremaphor ™ PS20 Ester (Polyoxyethylene Sorbitan Monolaurate available from BASF Corporation) | 90 | 1 |
| Proxel$^{RTM}$ Press paste (1,2-Benzisothiazolin-3-one available from Avecia Inc. | 10 | 2 |
| The components were mixed and then heated with further agitation at 50° C. until all of the BIT (Proxel$^{RTM}$) dissolved. This resulted in a dark amber solution. | | |

EXAMPLE 8b CONTINUED

| Components | Weight % | Order of addition |
|---|---|---|
| Mixture 2 | | |
| Vantocil$^{RTM}$ IB (20% solution of Polyhexamethylene biguanide hydrochloride available from Avecia Limited). | 71.1 | 1 |
| Mixture 1 | 28.6 | 2 |
| Surfynol ™ 104 PG (acetylenic diol available from Air Products and Chemicals Inc.) | 0.3 | 3 |
| Procedure: | | |
| Mixture 1 was added to Vantocil$^{RTM}$ IB stepwise with continued stirring, ensuring that the mixture was clear before the addition of another portion. Surfynol ™ 104 PG was also added. The complete addition of mixture 1 resulted in a clear dark brown solution. | | |

EXAMPLE 8c

Polyhexamethylene biguanide (PHMB) Hydrochloride (Vantocil® IB) and 2-methyl-4-isothiazolin-3-one (MIT) Formulation

| Components | Weight % | Order of addition |
|---|---|---|
| Vantocil ® IB (20% solution of Polyhexamethylene biguanide hydrochloride available from Avecia Limited). | 55.56 | 1 |
| Propylene Glycol (Available from Lyondell Chemical Company) | 33.33 | 2 |
| Kordek ™ 50C (a 50% composition of MIT available from Rohm & Haas) | 11.11 | 3 |
| Procedure: | | |
| Propylene glycol was added to the Vantocil ® IB with stirring. Kordek ™ 50C was then slowly added to the mixture with continued stirring which resulted in a clear light tan solution. | | |

EXAMPLE 8d

Polyhexamethylene biguanide (PHMB) Hydrochloride (Vantocil® IB) and CMIT/MIT Formulation

| Components | Weight % | Order of addition |
|---|---|---|
| Vantocil ® IB (20% solution of Polyhexamethylene biguanide (PHMB) hydrochloride available from Avecia Limited). | 64.1 | 1 |
| Propylene Glycol (available from Lyondell Chemical Company) | 25.6 | 2 |
| Kathon ™ WT (8.6% CMIT (5-chloro-2-methyl-4-isothiazolinone-3-one), 2.6% MIT (2-methyl-4-isothiazolin-3-one) available from Rohm & Haas) | 10.3 | 3 |

Procedure:

Propylene glycol was added to Vantocil ® IB with stirring. Kathon ™ WT was then added slowly to the mixture with further stirring. This resulted in the formation of a clear yellow solution

The invention claimed is:

1. A method for inhibiting the growth of micro-organisms in a latex comprising adding to the latex an effective amount of
   (a) a linear polymeric biguanide comprising a mixture of polymer chains in which the individual polymer chains, excluding the terminating groups, are of the Formula (7) or a salt thereof:

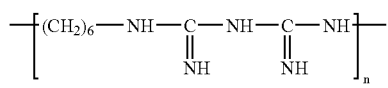

Formula (7)

wherein n is from 4 to 40; and
   (b) an isothiazolinone of the Formula (1) or a salt or complex thereof:

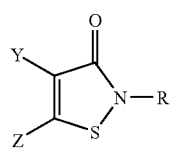

Formula (1)

wherein:
R is H or $C_{1-8}$-alkyl; and
Y and Z together with the carbon atoms to which they are attached form an optionally substituted 6 membered ring;
the combination of (a) and (b) having a fractional inhibitory concentration of less than one.

2. A method according to claim 1 wherein:
R is H, methyl, butyl or octyl; and
Y and Z together form an optionally substituted 6 membered ring.

3. A method according to claim 1 wherein the isothiazolinone of Formula (1) is a benzisothiazolinone of the Formula (2) or a salt or complex thereof:

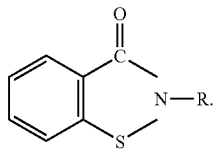

Formula (2)

4. A method according to claim 1 wherein the isothiazolinone is 1,2-benzisothiazolin-3-one.

5. A method according to claim 1 wherein the isothiazolinone is 2-n-butyl-1,2-benzisothiazolin-3-one.

6. A method according to claim 1 wherein the latex is a cationic or sterically stabilised latex.

7. A method according to claim 1 wherein the latex is substantially free from anionic compounds.

8. A method according to claim 1 wherein the latex is stabilised with a partially hydrolysed poly(vinylacetate) or a poly(vinylalcohol).

9. A method according to claim 1 wherein the latex is stabilised by a water-soluble colloid, and the latex is selected from:
   (i) a latex obtainable by emulsion co-polymerisation of methyl methacrylate with butyl acrylate, 2-ethylhexyl acrylate or ethyl acrylate;
   (ii) a polyvinylacetate latex; and
   (iii) a latex obtainable by emulsion polymerisation of vinyl acetate and ethylene.

10. A method according to claim 1 wherein the isothiazolinone and polymeric biguanide are added to the latex in the form of a composition comprising the isothiazolinone, the polymeric biguanide and optionally a medium.

11. A composition comprising a latex:
   (a) a linear polymeric biguanide comprising a mixture of polymer chains in which the individual polymer chains, excluding the terminating groups, are of the Formula (7) or a salt thereof:

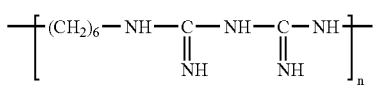

Formula (7)

wherein n is from 4 to 40; and (b) an isothiazolinone of the Formula (1) or a salt or complex thereof:

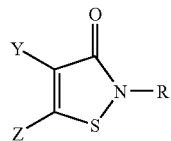

Formula (1)

wherein:

R is H or $C_{1-8}$-alkyl; and

Y and Z each independently are H, chlorine or $C_{1-4}$-alkyl or Y and Z together with the carbon atoms to which they are attached form an optionally substituted 6 membered ring;

the combination of (a) and (b) having a fractional inhibitory concentration of less than one.

12. An anti-microbial composition comprising:
(i) a linear polymeric biguanide which is a mixture of polymer chains in which the individual polymer chains, excluding the terminating groups, are of the Formula (7) or a salt thereof

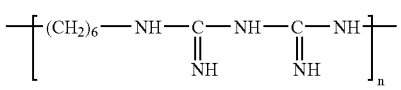

Formula (7)

wherein n is from 4 to 40; and (ii) a benzisothiazolinone derivative of the Formula (2) or a salt or complex thereof;

Formula (2)

wherein R is H or $C_{1-8}$-alkyl, the combination of (i) and (ii) having a fractional inhibitory concentration of less than one.

* * * * *